（12） United States Patent
Johnson et al.

(10) Patent No.: US 8,259,303 B2
(45) Date of Patent: Sep. 4, 2012

(54) OCT COMBINING PROBES AND INTEGRATED SYSTEMS

(75) Inventors: Bartley C. Johnson, North Andover, MA (US); Dale C. Flanders, Lexington, MA (US)

(73) Assignee: Axsun Technologies, Inc., Billerica, MA (US)

( * ) Notice: Subject to any disclaimer, the term of this patent is extended or adjusted under 35 U.S.C. 154(b) by 101 days.

(21) Appl. No.: 12/466,993

(22) Filed: May 15, 2009

(65) Prior Publication Data

US 2009/0284749 A1 Nov. 19, 2009

Related U.S. Application Data

(60) Provisional application No. 61/053,241, filed on May 15, 2008.

(51) Int. Cl.
G01B 9/02 (2006.01)
(52) U.S. Cl. .................................................... 356/479
(58) Field of Classification Search .................. 356/479, 356/497, 477
See application file for complete search history.

(56) References Cited

U.S. PATENT DOCUMENTS

| | | | |
|---|---|---|---|
| 7,415,049 B2 | 8/2008 | Flanders et al. | |
| 7,486,405 B2 * | 2/2009 | Hogan | 356/497 |
| 7,720,526 B1 * | 5/2010 | Modell | 600/476 |
| 2002/0093655 A1 | 7/2002 | Everett et al. | |
| 2004/0218189 A1 | 11/2004 | Izatt et al. | |
| 2005/0024646 A1 | 2/2005 | Quadling et al. | |
| 2006/0055936 A1 | 3/2006 | Yun et al. | |
| 2006/0079762 A1 | 4/2006 | Norris et al. | |
| 2006/0109478 A1 | 5/2006 | Tearney et al. | |
| 2006/0195019 A1 | 8/2006 | Premachandran et al. | |
| 2006/0241493 A1 | 10/2006 | Feldman et al. | |
| 2007/0024868 A1 | 2/2007 | Izatt et al. | |
| 2007/0081166 A1 * | 4/2007 | Brown et al. | 356/479 |
| 2007/0088219 A1 * | 4/2007 | Xie et al. | 600/473 |
| 2007/0134615 A1 | 6/2007 | Lovely | |
| 2007/0146726 A1 | 6/2007 | Quadling et al. | |
| 2007/0238955 A1 * | 10/2007 | Tearney et al. | 600/407 |
| 2008/0007734 A1 * | 1/2008 | Park et al. | 356/495 |
| 2008/0024788 A1 | 1/2008 | Shimizu et al. | |
| 2008/0049232 A1 | 2/2008 | Vakoc et al. | |
| 2008/0062429 A1 | 3/2008 | Liang et al. | |
| 2008/0090199 A1 * | 4/2008 | Noguchi et al. | 433/29 |
| 2008/0118886 A1 | 5/2008 | Liang et al. | |
| 2008/0186501 A1 | 8/2008 | Xie | |
| 2008/0194947 A1 | 8/2008 | Kokkelink et al. | |
| 2008/0228033 A1 * | 9/2008 | Tumlinson et al. | 600/112 |
| 2008/0252901 A1 | 10/2008 | Shimizu et al. | |

(Continued)

OTHER PUBLICATIONS

Meissner S., et al., "Investigation of Murine Vasodynamics by Fourier Domain Optical Coherence Tomography," Proc. of SPIE-OSA Biomedical Optics, SPIE, vol. 6627, 2007, pp. 66270D-1 to 66270D-10.

(Continued)

*Primary Examiner* — Tarifur Chowdhury
*Assistant Examiner* — Jonathan Hansen
(74) *Attorney, Agent, or Firm* — Houston & Associates, LLP (57) ABSTRACT

Optical coherence tomography (OCT) probe and system designs are disclosed that minimize the effects of mechanical movement and strain to the probe to the OCT analysis. It also concerns optical designs that are robust against noise from the OCT laser source. Also integrated OCT system-probes are included that yield compact and robust electro-opto-mechanical systems along with polarization sensitive OCT systems.

5 Claims, 9 Drawing Sheets

U.S. PATENT DOCUMENTS

| | | | |
|---|---|---|---|
| 2009/0018436 | A1 | 1/2009 | Gey Van Pittius et al. |
| 2009/0021745 | A1 | 1/2009 | Tamura |
| 2009/0046295 | A1* | 2/2009 | Kemp et al. .................. 356/479 |
| 2009/0069794 | A1 | 3/2009 | Kurtz |

OTHER PUBLICATIONS

Moon, S., et al., "Normalization detection scheme for high-speed optical frequency-domain imaging and reflectometry," Optics Express, vol. 15, No. 23, Nov. 12, 2007, pp. 15129-15146.

Popp, A., et al., "Imaging of the three-dimensional alveolar structure and the alveolar mechanics of a ventilated and perfused isolated rabbit lung with Fourier domain optical coherence tomography," Journal of Biomedical Optics, vol. 11 No. 1, Jan./Feb. 2006, pp. 014015-1 to 014015-9.

Tumlinson, A., et al., "Endoscope-tip interferometer for ultrahigh resolution frequency domain optical coherence tomography in mouse colon," Optics Express, vol. 14, No. 5, Mar. 6, 2006, pp. 1878-1887.

Partial Search Report dated Oct. 26, 2009, from counterpart International Application No. PCT/US2009/044179, filed on May 15, 2009.

U.S. Appl. No. 12/396,099, filed Mar. 2, 2009, entitled "Optical Coherence Tomography Laser with Integrated Clock," by Dale C. Flanders, et al.

International Preliminary Report on Patentability mailed Nov. 25, 2010, from International Application No. PCT/US2009/044179, filed on May 15, 2009.

* cited by examiner

OCT COMBINING PROBES AND INTEGRATED SYSTEMS

RELATED APPLICATIONS

This application claims the benefit under 35 USC 119(e) of U.S. Provisional Application No. 61/053,241, filed on May 15, 2008, which is incorporated herein by reference in its entirety.

BACKGROUND OF THE INVENTION

Optical coherence analysis relies on the use of the interference phenomena between a reference wave and an experimental wave or between two parts of an experimental wave to measure distances and thicknesses, and calculate indices of refraction of an object of interest. Optical Coherence Tomography (OCT) is one example technology that is used to perform usually high-resolution cross sectional imaging that can provide images of objects such as biological tissue structures, for example, on the microscopic scales in real time. Optical waves are sent through an object and a computer produces images of cross sections of the object by using information on how the waves are changed.

The original OCT imaging technique is the time-domain OCT (TD-OCT), which uses a movable reference mirror in a Michelson interferometer arrangement. Another type of optical coherence analysis is termed Fourier domain OCT (FD-OCT). Other terms are time encoded Frequency Domain OCT and swept source OCT. These techniques use either a wavelength swept source and a single detector, sometimes referred to as time-encoded FD-OCT or TEFD-OCT, or a broadband source and spectrally resolving detector system, sometimes referred to spectrum-encoded FD-OCT or SEFD-OCT. FD-OCT has advantages over time domain OCT (TD-OCT) in speed and signal-to-noise ratio (SNR).

TEFD-OCT has advantages over SEFD-OCT in some respects. The spectral components are not encoded by spatial separation, but they are encoded in time. The spectrum is either filtered or generated in successive frequency steps and reconstructed before Fourier-transformation.

Probe design is an important aspect of OCT system design, especially on systems that are intended to analyze the human body, such as medical diagnostic systems. On one hand, the probes must be mechanically robust to withstand use and possibly repeated use by medical care delivery personnel such as doctors, nurses and technicians in clinical settings. The probes should also be robust against noise generated from the use in their intended application. For example, OCT probe systems for intravascular analysis applications are typically long, extending from at least the point of access, such as the femoral artery to the coronary or carotid artery that is to be scanned. Moreover, the probes are often spun at high speed within a sheath while being pulled-back through the artery section of interest to generate a cylindrical scan. Any concomitant mechanical stress on the fiber can induce length changes and birefringence due to twisting. Probes for dental applications typically include a long umbilical that connects the handpiece/optical interface to the OCT analysis system or console; noise introduced in the OCT analysis due to mechanical shock to both the umbilical and handpiece/optical interface should be minimized.

SUMMARY OF THE INVENTION

The present invention concerns probe and OCT system designs that minimize noise and interference due to the effects of mechanical movement and strain on the OCT system. It also concerns optical designs that are robust against amplitude noise from the OCT laser source. In embodiments, this is achieved by combining the OCT signals from the reference arms and signals arms of the OCT interferometer in the handpiece itself. This combining is performed by fiber couplers that are easily integrated into compact handpieces and connected to scanning units and fiber reference arms. Thus, noise due to movement and stress to the system, such as to the umbilical that connects the analysis system to the probe, does not corrupt the OCT analysis and/or image since the noise is common and does not appear on only the reference or signal arms of the interferometer. In examples, amplitude referencing is performed and delay matched to the interference signals to compensate for the optical delay associated with the umbilical and other components. Also integrated OCT system-probes are included that yield compact and robust electro-opto-mechanical systems along with polarization sensitive OCT systems.

In general, according to one aspect, the invention features, an optical coherence tomography probe, comprising: a handpiece housing; an optical window in the handpiece housing; a reference arm reflector in the handpiece housing; an interference signal fiber coupler in the handpiece housing that receives an optical coherence tomography (OCT) signal from an OCT analysis system and divides the OCT signal between a reference optical fiber arm and a signal optical fiber arm; and an optical window in the handpiece housing through which the OCT signal from the signal optical fiber arm is transmitted to an object of interest and through which an object OCT signal is received from the object of interest and coupled into the signal optical fiber arm. The object OCT signal is mixed or combined with the OCT signal from the reference optical fiber arm that is reflected by the reference arm reflector to generate an interference signal that is transmitted from the handpiece housing to the OCT analysis system.

In general according to another aspect, the invention features an optical coherence tomography method. This method comprises receiving an OCT signal from an OCT analysis system in an interference signal fiber coupler located within a handpiece housing and dividing the OCT signal between a reference optical fiber arm and a signal optical fiber arm, transmitting the OCT signal on the signal optical fiber arm from the handpiece housing to an object of interest and receiving an object OCT signal from the object of interest into the handpiece housing and coupling the object OCT signal onto the signal optical fiber arm, combining the object OCT signal with the OCT signal from the reference optical fiber arm to generate an interference signal, and transmitting the interference signal from the handpiece housing to the OCT analysis system.

In general, according to still another aspect, the invention features an optical coherence tomography system. This system comprises a swept source laser for generating the OCT signal that is transmitted to a handpiece, a detector system that detects the interference signal received from the handpiece and a controller that uses the response of the detector system to generate an image of an object of interest.

In general, according to another aspect, the invention features, an integrated optical system for detecting an interference signal generated by an OCT probe. The integrated optical system comprises an hermetic package, an optical bench in the hermetic package, a detector system attached to the bench for detecting the interference signal, and a beam splitter system attached to the bench that couples an OCT signal from a swept laser source to the OCT probe and couples the interference signal from the OCT probe to the detector system.

In general, according to another aspect, the invention features, an integrated OCT system. The system comprises a hermetic package having an optical window, an optical bench in the hermetic package, a swept source laser system attached to the optical bench for generating an OCT signal, a detector system attached to the bench for detecting an interference signal. A beam splitter system is attached to the bench that couples the OCT signal from the swept laser source through the optical window to an object of interest, couples a portion of the OCT signal to a reference arm, couples light returning from the reference arm to the detector system, and directs light returning from the object of interest to the detector system.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
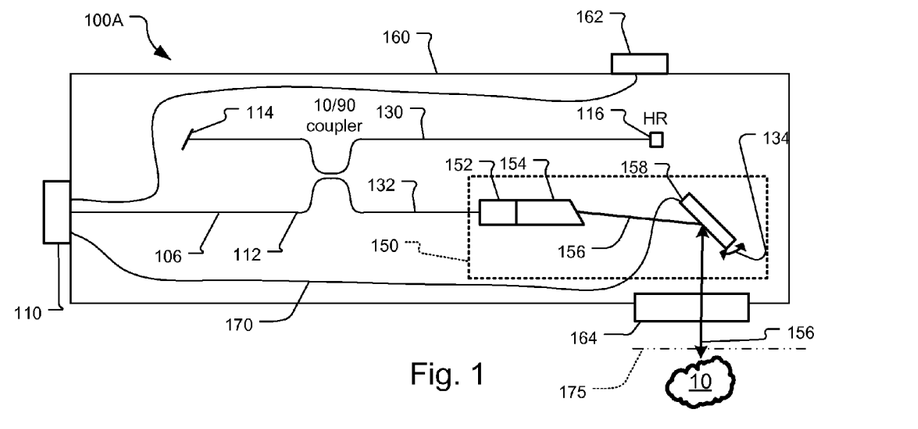
FIG. 1 is a schematic view of an optical coherence tomography (OCT) probe according to a first probe embodiment of the present invention.

FIG. 1 shows an optical coherence tomography (OCT) probe 100A that has been constructed according to the principles of the present invention (first probe embodiment).

Generally, the probe 100 comprises a handpiece housing 160. This handpiece housing is typically grasped by an operator of the OCT system. It is characterized by a rigid portion that connects to an OCT analysis unit by an intervening flexible or articulated umbilical.

The housing 160 comprises an optical window element 164, which is typically tilted and anti-reflection coated to prevent spurious reflection back into the OCT system. This optical window element 164 is transmissive to the optical frequencies at which the OCT system operates. In one example, the OCT system operates in the near infrared. In some embodiments, the optical window 164 is also transmissive to visible optical frequencies to enable a visible targeting beam to pass through the window to indicate where the non-visible infrared OCT signal is impinging on the object of interest 10.

The handpiece 160 in one implementation includes an electro-optical connector 110. This electro-optical probe connector 110 enables operator connection to and disconnection from an OCT analysis system. In one example, the electro-optical probe connector 110 provides the OCT and interference signals between the probe system 100 and the analysis system along with electrical control signals.

In other embodiments, the umbilical is integral with the probe such that the connector 110 is not used.

In more detail, the OCT signal, such as light from a swept source laser, is received from the OCT analysis system via the connector 110 and coupled onto an OCT/interference signal optical fiber 106. The OCT/interference signal fiber 106 couples the OCT signal received from the OCT analysis system to an interference/OCT signal coupler 112. In one example, the interference/OCT signal coupler 112 is a 90/10 percent fiber coupler, and thus does not divide the light evenly between the two output ports. Specifically, the interference/OCT signal coupler 112 provides the OCT signal received on the OCT/interference signal fiber 106 to a reference arm optical fiber 130 and a signal arm optical fiber 132, with most of the light, i.e., 90% or greater, in this current example, on the signal arm optical fiber 132.

The reference arm optical fiber 130 forms the reference arm of an interferometer that is implemented, preferably entirely, within the handpiece housing 160. Specifically, the reference arm optical fiber 130 terminates in a reflector 116. In one example, the reflector 116 is simply a highly reflective coating at the end of the reference arm optical fiber 130. Exemplary highly reflective coatings include dielectric stack coatings and metalized endfacet coatings that are deposited on the endfacet of the reference arm optical fiber 130. In other examples, the reflector 116 is implemented as a discrete mirror element, and possibly including a discrete lens to collimate and couple light between the endfacet of the reference arm optical fiber 130 and the mirror reflector.

The signal arm optical fiber 132 transmits the received OCT signal to a scanning unit 150. The scanning unit 150 couples the OCT signal between the object of interest 10 and the signal arm optical fiber 132.

In the illustrated embodiment, the scanning unit 150 comprises an optional glass or transmissive spacer 152 that is secured to the endfacet of the signal arm optical fiber 132. This spaces the endfacet of the signal arm optical fiber 132 from a GRIN (graded refractive index) lens element 154, which has an angled output facet to prevent parasitic reflections. The GRIN lens 154 focuses the OCT signal from the signal arm optical fiber 132 onto the sample 10. The freespace light beam 156 is directed to a fold mirror 158 that directs the OCT signal beam 156 through the optical window 164 to the object of interest 10. Then light returning from the object of interest 10 is coupled back through the optical window 164 to reflect off of the fold mirror 158 and be coupled back into the signal arm optical fiber 132 via the GRIN lens 154 and the spacer element 152.

In a preferred embodiment, the fold mirror 158 is a scanning mirror. Specifically, it is driven to both tip and tilt in the x and y axes as indicated by arrow 134. In one implementation, this is a micro electro mechanical system (MEMS) mirror that scans the OCT signal beam 156, such as raster scans, over the object of interest 10 in order to generate a three-dimensional image of the object of interest 10.

In the typical embodiment, the handpiece housing 160 also supports one or more electrical control switches 162. These control switches 162 are coupled to the OCT analysis system via the opto-electrical connector 110 via control line 170. The switches are used by the operator to begin and end OCT scanning and activate a visible targeting laser during the OCT analysis of the object of interest 10. Preferably, the switches 162 are also used to electronically drive and control the scanning mirror 158.

The light returning from the object of interest 10 on the signal arm optical fiber 132 is combined with the light returning from the reflector 116 on the reference arm optical fiber 130 in the interference/OCT signal coupler 112. This combination generates the interference signal that is transmitted to the OCT analysis system on the OCT/interference signal optical fiber 106 via the electro-optical connector 110.

Since the typical fiber coupler is a four port system, some interference signal light is also coupled onto the fourth arm that terminates in the termination 114. This light is lost in this exemplary embodiment. Otherwise, a three-port coupler is used in other implementations. The length of the reference arm optical fiber 130 is important to control the scanning depth in the object. Specifically, the length of the reference arm optical fiber 130 is sized so that plane 175 is the zero distance virtual reference plan of the OCT system. Thus, the optical path length of the reference arm optical fiber 130 is made equal to the sum of the optical path lengths of the signal arm optical fiber 132, transmissive spacer 152, GRIN lens element 154, and the free space path to the reference plane 175, including window 164.

The length of the reference arm optical fiber 130 is important to control the scanning depth in the object. Specifically, the length of the reference arm optical fiber 130 is sized so that plane 175 is the zero distance virtual reference plan of the OCT system. Thus, the optical path length of the reference arm optical fiber 132 is made equal to the sum of the optical path lengths of the signal arm optical fiber 132, transmissive spacer 152, GRIN lens element 154, and the free space path to the reference plane 175, including window 164.

The probe 100 in some sense a "common path" probe, with one fiber connection back to the OCT system. It would typically be used with some sort of relative intensity noise (RIN) reduction system. One option is to use a balanced receiver to accept input from the probe in one detector and a laser amplitude signal in the other (US2009/0046295 A1, Kemp, et al., Feb. 19, 2009, FIG. 13). Another option is to ratio the probe signal with that of a laser power monitor (Normalization detection scheme for high-speed optical frequency-domain imaging and reflectometry, Sucbei Moon and Dug Young Kim, 12 Nov. 2007/Vol. 15, No. 23/OPTICS EXPRESS 15129).

Figure 2:
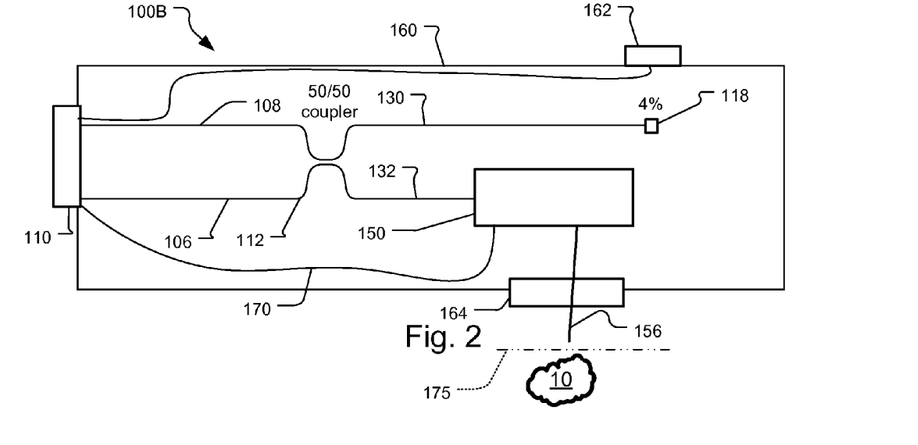
FIG. 2 is a schematic view of an OCT probe according to a second probe embodiment of the present invention.

FIG. 2 shows a second embodiment of the OCT probe 100B. This embodiment is generally similar to the first probe embodiment but uses two OCT/interference signal fibers 106, 108 to optically connect the OCT probe 100 to the OCT analysis system. This probe is compatible with standard balanced receiver/relative intensity noise (RIN) reduction scheme, and would also suppress autocorrelation artifacts from the sample signal interfering with itself.

In more detail, the OCT signal from the OCT analysis system is received via the electro-optical connector 110 typically through a flexible umbilical on a first OCT/interference signal fiber 106 and a second OCT/interference signal fiber 108, or only one of these fibers.

The light is then coupled to via a 50/50 interference/OCT signal coupler 112 between the reference arm optical fiber 130 and the signal arm optical fiber 132.

The OCT signal on the reference arm optical fiber is transmitted to a partial reflector 118. In one example, this partial reflector reflects back less than 10%, such as 4% or less, of the OCT signal light that carried on the reference arm optical fiber 130. In one example, this partial reflector 118 is implemented as a dielectric stack or metal coating on the endfacet of the optical fiber 130.

Light on the signal arm optical fiber 132 is transmitted to the scanning unit 150. This directs the light as described previously through the optical window 164 to the object of interest 10. Returning light in turn passes through the optical window 164 and is coupled by the scanning unit 150 to the signal arm optical fiber 132.

The OCT signal returning on the reference arm optical fiber 130 and the light from the object of interest returning on the signal arm optical fiber 132 is combined in the 50/50 interference/OCT signal coupler 112. This combination generates the interference signal that is transmitted back to the OCT analysis system on the first and second OCT/interference signal fibers 106, 108 via the electro-optical connector 110.

Figure 3:
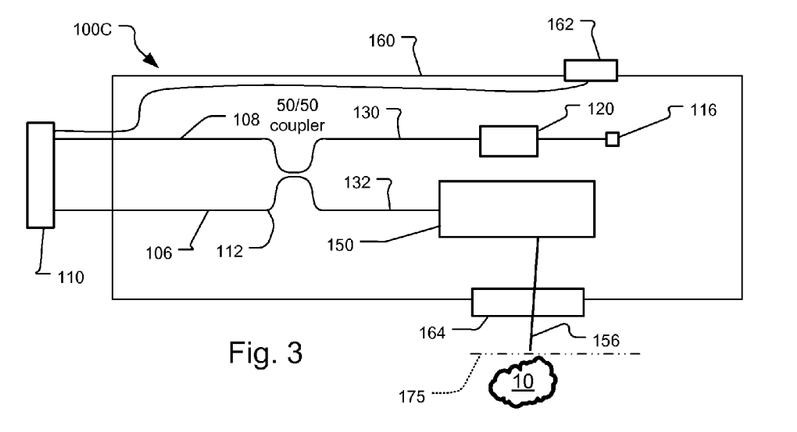
FIG. 3 is a schematic view of an OCT probe according to a third probe embodiment of the present invention.

FIG. 3 shows a third embodiment of the OCT probe system 100C. This embodiment is similar to the second embodiment OCT probe system of FIG. 2. The difference lies in the configuration of the reference arm. In this example, the reference arm optical fiber 130 includes an attenuator 120 that attenuates the OCT signal carried on the reference arm optical fiber 130. The light passing through the attenuator 120 is then reflected by a highly reflecting endfacet 116. This highly reflecting end facet is typically implemented as described in connection with the first probe embodiment of FIG. 1. The OCT light returning from the reflector 116 passes through the attenuator 120 and then on the reference arm optical fiber 130 to the interference/OCT signal coupler 112.

The potential problem associated with the embodiment of FIG. 2 is dissipating the light that is transmitted through the partial reflector 118. This transmitted light is then potentially within the handpiece housing 116 and can potentially serve as an interference source: either being coupled back into the reference arm optical fiber 130 creating multipath interference or possibly interfering with the OCT signal that is transmitted to and from the object of interest 10. This potential problem is addressed in the embodiment of FIG. 3 by using the attenuator 120 to absorb the excess OCT signal light in the reference arm to ensure that it does not create interference. In examples, the attenuator 120 is a lossy element that is implemented by fiber microbending, through a lossy fiber splice, or other means.

Figure 4:
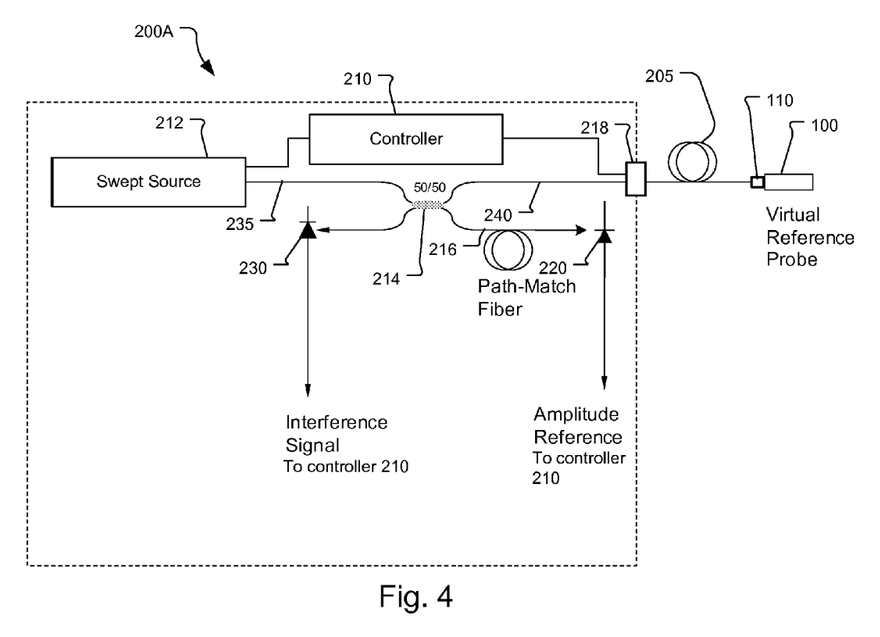
FIG. 4 is a schematic view of an OCT system according to a first system embodiment of the present invention.

FIG. 4 illustrates an OCT analysis system 200A that is compatible with the OCT probe of FIG. 1. Specifically, the OCT analysis system 200A provides electrical and optical connection to the probe 100 via a typically flexible or articulated umbilical 205. Specifically, this umbilical extends between an OCT analysis system electro-optical connector 218 and the probe connector 110. This flexible umbilical 205 allows the reference probe 100 to be moved around the object of interest, such as the patient, to enable analysis of regions of interest of the patient, such as the patient's teeth or skin in some examples.

The OCT signal receive by the probe 100 is generated in the preferred embodiment by a swept laser source 212. An exemplary source is that described in U.S. patent application Ser. No. 12/396,099, filed on 2 Mar. 2009, entitled Optical Coherence Tomography Laser with Integrated Clock, by Flanders, et al., which is incorporated herein by this reference.

The OCT signal generated by the swept source laser is transmitted to a 50/50 OCT/amplitude reference fiber coupler 214 on a swept source optical fiber 235. The 50/50 coupler 214 divides the OCT signal from the swept source 212 between an amplitude reference fiber 216 and the OCT probe optical fiber 240. This OCT probe optical fiber 240 transmits the OCT signal from the 50/50 coupler 214 to the unit connector 218. Similarly, the returning interference signal from the reference probe 100 is received via the unit connector 218 on the probe optical fiber 240 and is then divided by the 50/50 OCT/amplitude reference fiber coupler 214.

The path match optical fiber 216 has a length that corresponds to twice the optical delay between the OCT/amplitude reference fiber coupler 214 and the reference probe 110 plus the delay from coupler 214 to interference signal photodiode detector 230. In this way, the delay induced by the path match optical fiber is consistent with the combined delay associated with OCT signal to the probe 100 and the interference signal returning on optical fiber 240 from the probe. The OCT signal light transmitted through the path match optical fiber 216 is then detected by an amplitude reference photodiode detector 220 which is then sampled by the controller 210 and used to remove amplitude noise in the system from the swept source 212.

The interference signal returning from the OCT probe 100 and received on OCT probe optical fiber 240 is transmitted through the 50/50 OCT/amplitude reference fiber coupler 214 to the interference signal detector 230. This detector detects that light which is then sampled by the controller 210.

In one example, the amplitude reference detector 220 and the interference detector 230 are combined into a balanced detector system for rejection of the amplitude noise from the swept source 212 in the interference signal. In this case, the optical power levels at the two detectors need to be balanced (For example, see a similar RIN reduction scheme in US2009/0046295 A1, Kemp, et al., Feb. 19, 2009, FIG. 13). Alternately, the signal from the amplitude reference detector 220 can be digitally divided in the controller 212, for example, by the interference signal from detector 230 for RIN reduction (Normalization detection scheme for high-speed optical frequency-domain imaging and reflectometry, Sucbei Moon and Dug Young Kim, 12 Nov. 2007/Vol. 15, No. 23/OPTICS EXPRESS 15129).

Figure 5:
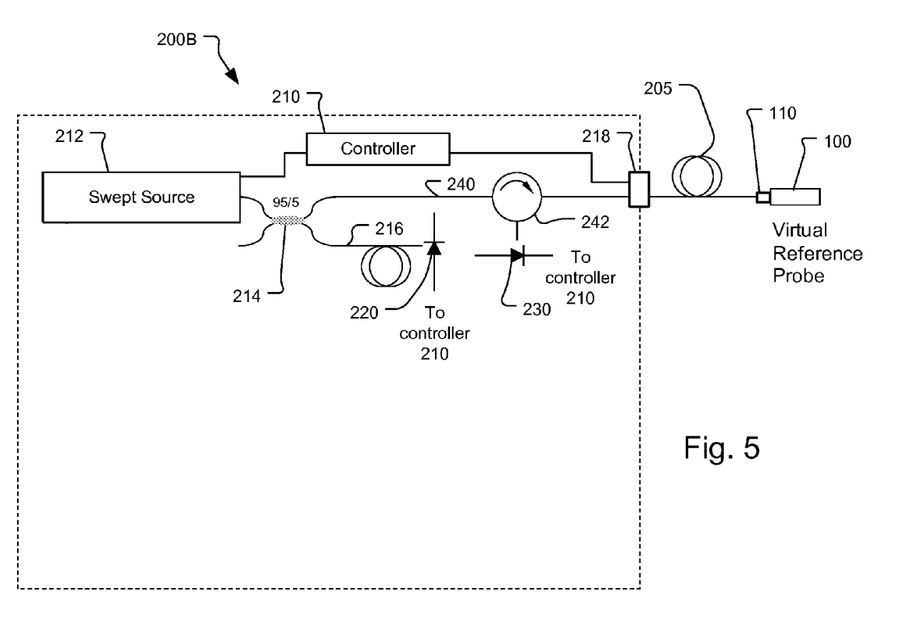
FIG. 5 is a schematic view of an OCT system according to a second system embodiment of the present invention.

FIG. 5 illustrates a second system embodiment 200B of the OCT analysis system that is also compatible with the probe of FIG. 1. This system makes more efficient use of the available optical power, but has more expensive components.

The second embodiment 200B uses an unbalanced OCT/amplitude reference fiber coupler 214 to divide the OCT signal from the swept source 212 between the amplitude reference path match fiber 216 and OCT probe optical fiber 240. The OCT signal light on the OCT probe optical fiber 240 passes through interference signal circulator 242 to be transmitted to the reference probe 100 via the unit electro-optical connector 218. In turn, the interference signal returning from the reference probe 100 is directed by the circulator 242 to interference signal detector 230.

The use of the circulator 242 leads to a more optically efficient system relative to FIG. 4 since the 95/5% OCT/amplitude reference fiber coupler 214 of this embodiment allows most of the OCT signal, greater than 90% and preferably 95% or more, generated by the swept source 212 to be directed to the object of interest with only a small amount being used to generate the amplitude reference.

Figure 6:
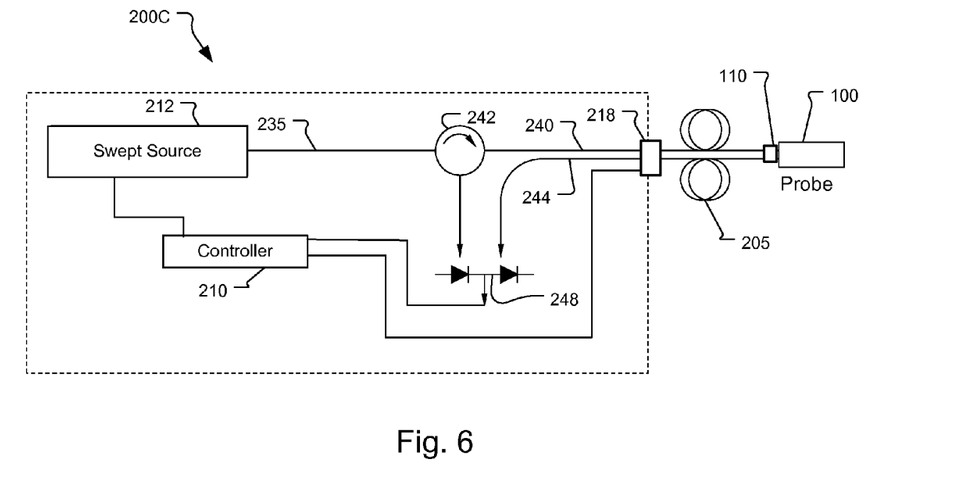
FIG. 6 is a schematic view of an OCT system according to a third system embodiment of the present invention.

FIG. 6 illustrates a third embodiment 200C of the OCT analysis system that is compatible with the probes of FIGS. 2 and 3. In this example, the OCT signal generated by the swept source 212 is transmitted on swept source optical fiber 235 to interference signal circulator 242 and then on OCT probe optical fiber 240 to the optical probe 100 via the unit connector 218. The interference signal from the OCT probe is then received on interference signal optical fiber 244 and the OCT probe optical fiber 240. The returning interference signal light on OCT probe optical fiber 240 is directed by the interference signal circulator 242 to the balanced detector 248. The interference signal received on the interference signal optical fiber 244 is directly coupled to the balanced detector 248

The balanced receiver reduces the effect of RIN on the system's signal-to-noise ratio. The common-path probe systems in FIGS. 4 and 5 also have methods to reduce the effects of RIN. A major advantage of the two-fiber probe (FIGS. 2 and 3) and the corresponding system (FIG. 6) is that the autocorrelation image (sample light interfering with itself) is strongly attenuated.

In implementations, the balanced receiver 248 is an auto-balanced receiver (one example is manufactured by New Focus. Part number 2017), which automatically balances the electrical signals from the two detectors even in the presence of mismatched lightwave signals impinging on the two detectors.

Figure 7:
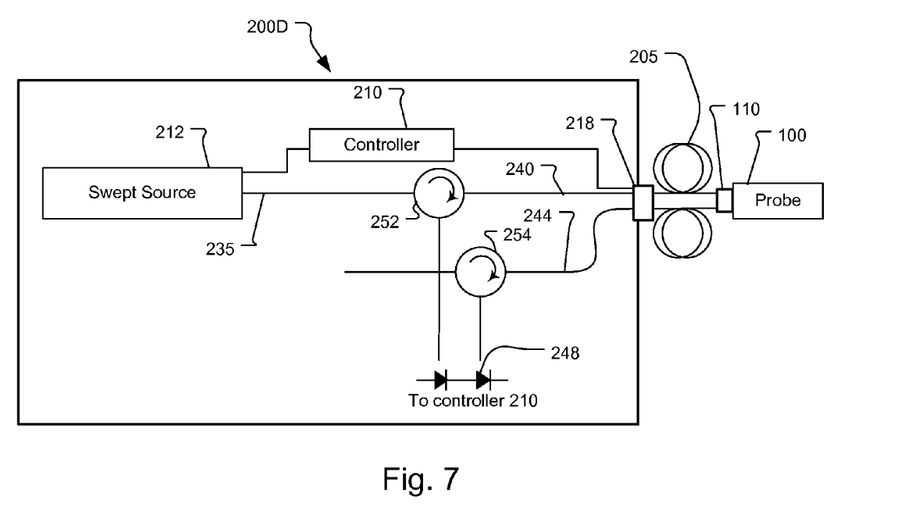
FIG. 7 is a schematic view of an OCT system according to a fourth system embodiment of the present invention.

FIG. 7 illustrates a variant, fourth embodiment 200B of the OCT system that uses two circulators 252, 254 for the two fiber probe embodiments. This configuration is similar to that in FIG. 6, except that it incorporates a "dummy" circulator 254 (one port not used) to help balance the lightwave signals present at the two detectors of the balanced receiver 248. If closely matched, the interference signal circulators 252, 254 will have similar optical losses vs. wavelength and balance the lightwave signals to the two detectors. A better match provides improves signal-to-noise performance and attenuation of the autocorrelation image. Better matching by the additional circulation may be preferred to the use of an auto-balanced detector for cost and performance reasons.

Figures 8A, 8B:
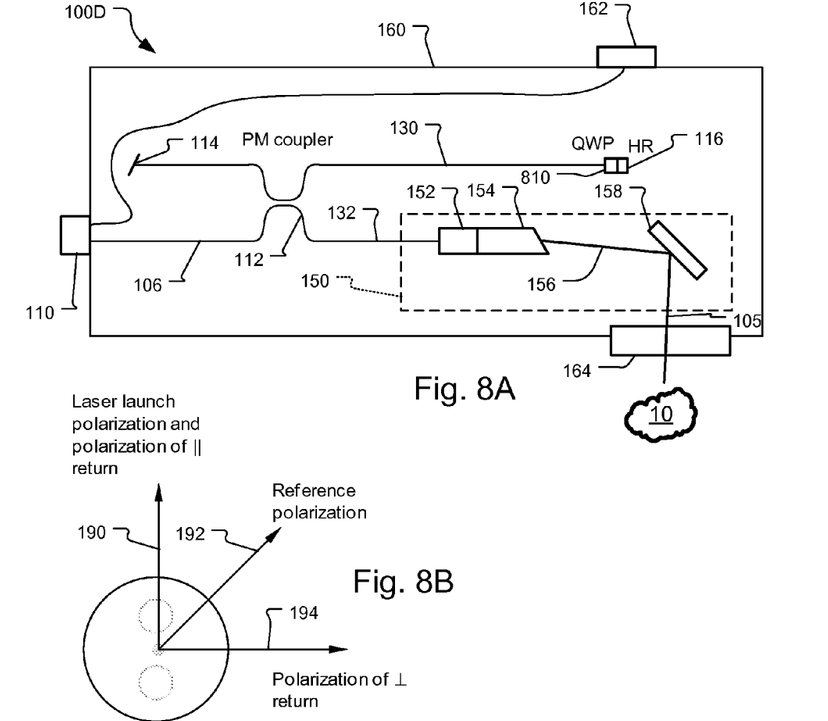
FIG. 8A is a schematic view of an OCT probe that provides for polarization sensitivity according to a first polarization probe embodiment of the present invention.
FIG. 8B illustrates the polarization of input signal, reference signal and return signals.

FIG. 8A illustrates a first polarization sensitive embodiment 100D of the OCT probe 100. Generally, this OCT probe is similar to the first probe embodiment of FIG. 1, thus, the descriptions associated with FIG. 1 are relevant here. This probe 100D, however, allows for polarization dependent or sensitive OCT analysis. Specifically, it enables the analysis of the OCT signal and the polarization characteristics of the object of interest 10.

In more detail, the OCT signal received on the OCT/Interference signal fiber 106 is a highly polarized signal such as a signal from a semiconductor external cavity laser system. To preserve polarization, the OCT/Interference signal fiber 106 is polarization maintaining optical fiber.

Specifically, as illustrated in FIG. 8B, the polarization of the swept source OCT signal is polarized according to one, slow, axis of the polarization maintaining (PM) fiber 106 that is used for the OCT/Interference signal fiber 106. See polarization 190.

The polarized OCT signal is divided by the interference/OCT signal coupler 112, which is a 50/50 polarization-maintaining coupler. The polarized OCT light is transmitted over the reference arm optical fiber 130, which is PM fiber, to the reflector 116. In this embodiment, there is an intervening quarter wave plate 810. This rotates the polarization of the light by 22½ degrees. As a result, the returning OCT signal light has both a portion that is polarized parallel to the input OCT signal but also perpendicular to the input OCT signal, see polarization 192 in FIG. 8B.

The OCT light that is transmitted through the PM interference/OCT signal coupler 112 onto the signal arm optical fiber 132, which is PM optical fiber, is directed to the object of interest 10 as described previously via the scanning system 150.

Light returning from the object of interest 110, however, now is potentially polarized according to the birefringence properties of the object of interest 10 and thus will have polarizations aligned along axis 190 and also fast axis 194, see FIG. 8B. Thus, the signal light returning from the object of interest 10 is then combined with the two polarizations returning from the reference arm optical fiber 130 by the PM coupler 112. Thus, this light then returns on the OCT signal/interference signal optical fiber 106 to the OCT analysis system. Interference signal now has two polarizations allowing for the polarization dependent OCT analysis of the object of interest.

Figure 8C:
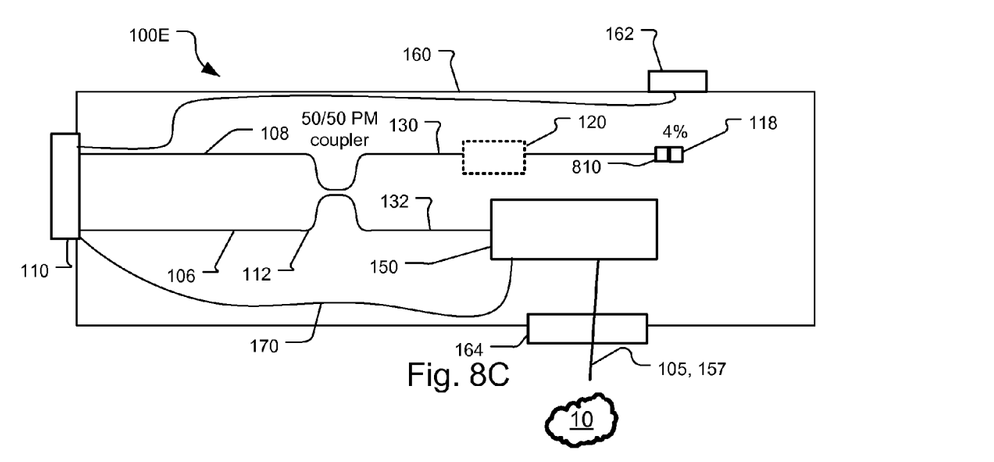
FIG. 8C is a schematic view of an OCT probe that provides for polarization sensitivity according to a second polarization probe embodiment of the present invention.

FIG. 8C shows a second embodiment polarization sensitive probe 100E that is analogous to the two fiber probes of FIGS. 2 and 3 and is compatible with standard balanced receiver/relative intensity noise (RIN) reduction scheme, and would also suppress autocorrelation artifacts from the sample signal interfering with itself.

In more detail, the OCT signal from the OCT analysis system on a first OCT/interference signal fiber 106 and a second OCT/interference signal fiber 108, or only one of these fibers. These fibers are PM fiber.

The light is then coupled to via a 50/50 interference/OCT signal PM fiber coupler 112 between the reference arm optical fiber 130 and the signal arm optical fiber 132, which are both constructed of PM fiber.

The OCT signal on the reference arm optical fiber 130 is transmitted to a partial reflector 118. In one example, this partial reflector reflects back less than 10%, such as 4% or less, of the OCT signal light that carried on the reference arm optical fiber 130. Alternatively, attenuator 120 is used in combination with a highly reflecting reflector. In either case, the intervening quarterwave plate 810 shifts the polarization so that the returning OCT signal now has component polarizations along each axis of the PM fiber.

Light on the signal arm PM optical fiber 132 is transmitted to the scanning unit 150. This directs the light as described previously through the optical window 164 to the object of interest 10. Returning light in turn passes through the optical window 164 and is coupled by the scanning unit 150 to the signal arm PM optical fiber 132.

The OCT signal returning on the reference arm optical fiber 130 and the light from the object of interest returning on the signal arm optical fiber 132 is combined in the 50/50 interference/OCT PM fiber coupler 112. This combination generates the interference signal for each polarization that is transmitted back to the OCT analysis system on the first and second OCT/interference PM fibers 106, 108 via the electro-optical connector 110.

Figure 9:
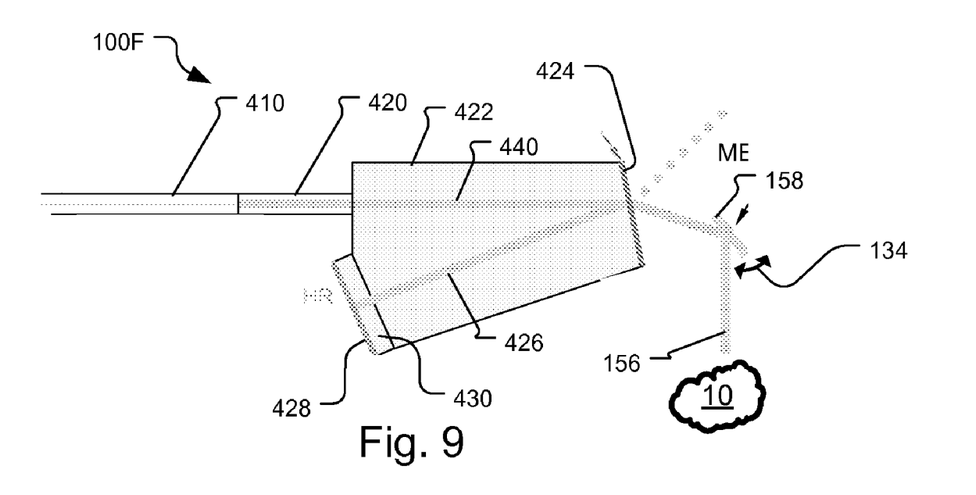
FIG. 9 is a plan view of the optical components of an OCT probe including an integrated reference path.

FIG. 9 illustrates an OCT probe 100F that includes an integrated reference arm. In this example, the OCT signal from the swept source laser is transmitted on an OCT/Interference signal optical fiber 410. The OCT signal is coupled to the probe body 422. In a preferred implementation, an intervening graded index fiber 420 connects the OCT/Interference signal optical fiber 410 to the probe body 422. The graded index fiber 420 collimates the OCT signal so that the beam 440 that is transmitted through the optical probe body 422 is collimated. The light passes through interface 424 to be directed to a scanning fold mirror 158, which scans see arrow 134. This allows the OCT signal beam 156 to be scanned over the object of interest 10.

Light returning from the object of interest is directed by the scanning fold mirror 158 through interface 424 to be directed back into the OCT/interference signal fiber 410 via the graded index fiber 420.

The probe body 422 includes an integrated reference arm. Specifically, the interface 424 is a partial reflector so that a portion, typically less than 10%, of the OCT signal beam 440 is directed to a reference arm that is within the transmissive probe body 422 to be directed to an interface 428 that has a high reflecting coating on it. This reflects light back to the interface 422 to mix or combine with the light returning from the object of interest to generate the interference signal that is then coupled via the graded index fiber 420 to the OCT/Interference signal fiber 410.

In one embodiment, this integrated OCT probe performs polarization dependent OCT analysis. In this example, a quarterwave plate 430 is attached to the probe body 422 to the interface 428 to rotate the light so that the light is now polarized along both axes. The OCT/interference signal fiber 410 is then polarization maintaining fiber.

Figure 10A:
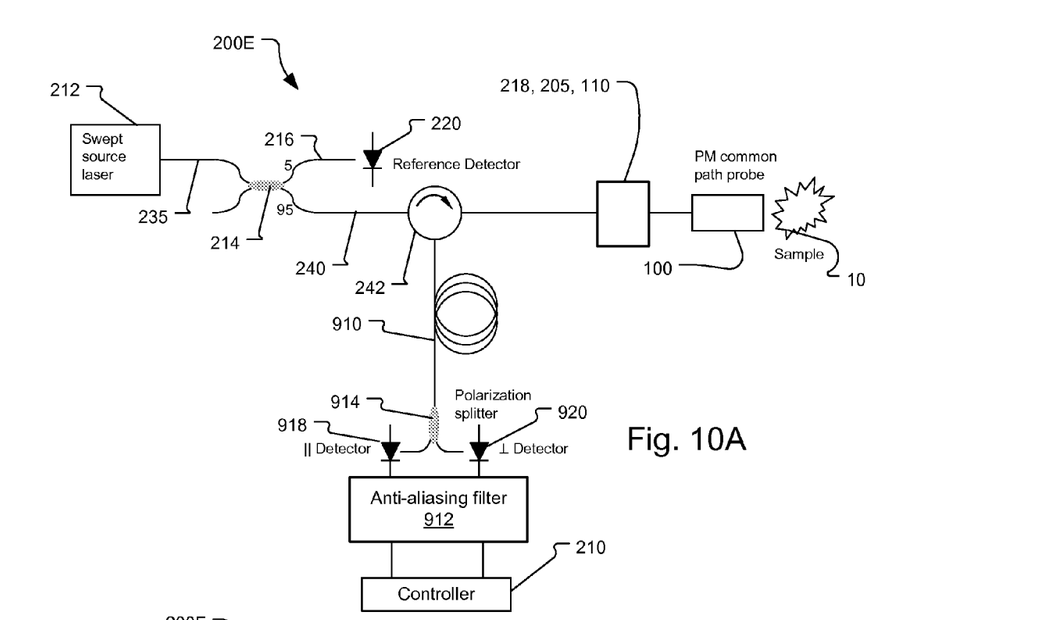
FIG. 10A is a schematic view of a polarization sensitive OCT system according to a first polarization system embodiment of the present invention.

FIG. 10A shows a first embodiment of a swept source polarization sensitive OCT system 200E that is compatible with the polarization sensitive, common path probes of FIGS. 8A and 9. In this embodiment, all of the optical fibers in the system are polarization maintaining.

In more detail, the swept source laser 212, provides a linearly polarized output aligned to the slow axis of the PM fiber of the system and specifically the PM fiber used for the swept source optical fiber 235. The OCT/amplitude reference fiber coupler 214 is similarly a PM fiber coupler that divides light between the amplitude path match fiber 216 and the OCT probe PM fiber 240. Preferably the OCT/amplitude reference fiber coupler 214 is an unbalanced coupler so that most of the OCT signal is transmitted to the sample, i.e., greater than 90% and preferably 95% or more. The OCT signal light on the OCT probe optical fiber 240 passes through interference signal circulator 242 to be transmitted to the reference probe 100 via the OCT probe optical fiber 240 and potentially a unit optical connector 218, umbilical 205, and probe connector 110.

In turn, the interference signal returning from the reference probe 100 is directed by the circulator 242 through a length of detector PM optical fiber 910. This fiber has a long length so that mixing of the parallel polarized light and the perpendicular light occurs at a frequency that is cut by an anti-aliasing filter 912 between the optical detectors 918, 920 and the analog-to-digital converters of the controller 210 that are used to sample the detector signals. For example, if the anti-alias filter removes any OCT image information at displacements greater than 5 mm, the fiber must be long enough that returns for the slow and fast axis light are separated >5 mm over the propagation distance. A typical fiber length is tens of meters for a few m of displacement.

An interference signal polarization splitter 914, which can be implemented with fiber-optic components or bulk optic components, separates the two signals of different polarizations and routes them to separate detectors, a parallel polarization detector 918 and a perpendicular polarization detector 920.

The system controller 210 generates and displays two images by separately processing the interference signals of the two polarizations: One where the light scattered from the sample 10 has the same polarization as the illumination light generated by the swept source laser 212, the parallel light; and a second image where the scattered light is polarized perpendicular to the illumination light.

Figure 10B:
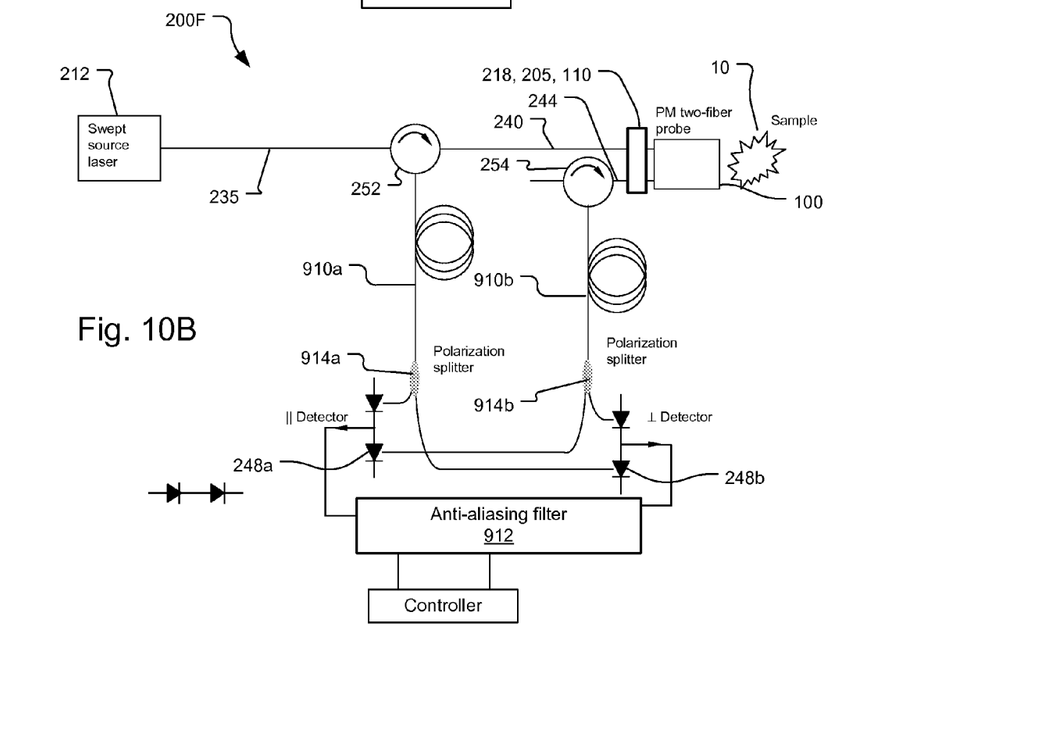
FIG. 10B is a schematic view of a polarization sensitive OCT system according to a second polarization system embodiment of the present invention.

FIG. 10B shows a polarization sensitive OCT analysis system 200F that is compatible with the polarization dependent, two-fiber probe of FIG. 8C.

In this example, the OCT signal generated by the swept source 212 is transmitted on swept source optical fiber 235 to interference signal circulator 252 and then on OCT probe optical fiber 240 to the optical probe 100, via potentially a unit optical connector 218, umbilical 205, and probe connector 110. The interference signal from the OCT probe is then received on interference signal optical fiber 244 and the OCT probe optical fiber 240. Returning interference signal light on OCT probe optical fiber 240 is directed by the circulator 252 to the detectors. The interference signal received on the interference signal optical fiber 244 directed to the detectors by circulator 254.

Similar to the embodiment of FIG. 10A, long lengths of PM fiber 910a, 910b are used on the optical paths to the detectors to prevent cross mixing of the parallel and perpendicular waves. On the other hand, the PM detector fibers 910a, 910b should have matched lengths.

A first interference signal polarization splitter 914a separates the polarizations of the interference signal received from interference signal circulator 252. A second interference signal polarization splitter 914b separates the polarizations of the interference signal received from interference signal circulator 254.

The perpendicular polarization interference signals from each splitter 914a, 914b are detected by a perpendicular balanced detector 248b and the parallel polarization interference signals are detected by parallel polarization balanced detector 248a.

This system has the RIN reduction and autocorrelation image suppression properties of the polarization insensitive systems of FIGS. 2 and 3, because of the use of balanced detection. The PM fibers 910a and 910b would have to be long to prevent polarization mixing as described above. They need to be roughly matched in length, so that the propagation delay difference is much less than the reciprocal of the highest electrical frequency generated in the detector systems.

Figure 11A:
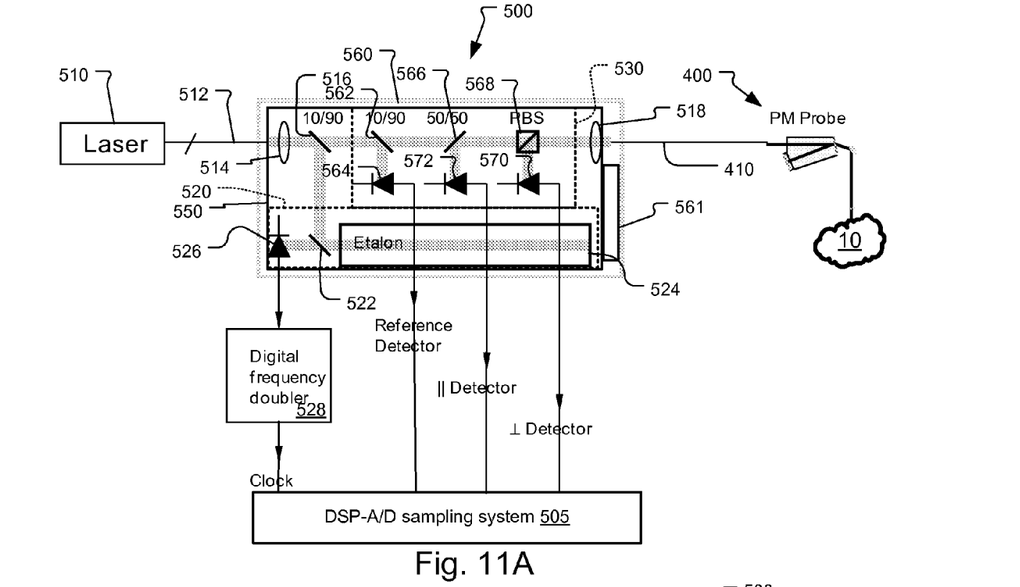
FIG. 11A is a schematic plan view of an integrated OCT engine according to the present invention.

FIG. 11A shows an integrated polarization dependent OCT system 500 that has been constructed according to the principals of the present invention and is compatible with the OCT probes of FIGS. 8A and 9.

Generally the integrated polarization dependent OCT system 500 comprises a tunable swept source laser subsystem 510, which generates a wavelength or frequency tunable optical signal, a clock subsystem 520, which generates k-clock signals at spaced frequency increments as the OCT signals or emissions of the laser 510 are spectrally tuned over a spectral scan band, and a detector subsystem 530, which includes an amplitude references and interference signal detectors. The k-clock signals are used to trigger sampling, typically in an OCT sampling analog to digital converter (A/D) system 505.

The detector subsystem 530 and clock subsystem 520 of the integrated polarization dependent OCT system 500 are integrated together on a common optical bench 550. This bench is termed a micro-optical bench and is typically less than 20 millimeters (mm) by 30 mm in size, and preferably less than 10 millimeters (mm) by 20 mm in size so that it fits within a standard butterfly or DIP (dual inline pin) hermetic package 560. In one implementation, the bench is fabricated from aluminum nitride. A thermoelectric cooler 561 is preferably disposed between the bench 550 and the package 560 (attached/solder bonded both to the backside of the bench 550 and inner bottom panel of the package 560) to control the temperature of the bench 550.

To collect and collimate the OCT signal light exiting from polarization maintaining fiber 512 from the tunable laser 510, an input lens structure 514 is used. Preferably, the input lens structure 514 comprises a LIGA mounting structure, which is deformable to enable post installation alignment, and a transmissive substrate in which the lens is formed. The transmissive substrate is typically solder or thermocompression bonded to the mounting structure, which in turn is solder bonded to the optical bench 550.

The input lens structure 514 couples the light from the laser 510 to a partially reflecting 10/90 substrate that functions as input beam splitter 516. A majority of the beam enters the detector subsystem 530 and the remaining beam is directed to the clock subsystem 520. In one example, greater than 90% of the input beam from the laser 510 is directed to the detector subsystem 530.

The OCT signal light is divided in the clock subsystem by a clock beam splitter 522, which is preferably a 50/50 splitter. The clock beam splitter 522 divides the light between to a clock etalon 524 and a k-clock detector 526. Any light not reflected by the splitter 522 is directed to a beam dump component that absorbs the light and prevents parasitic reflections in the hermetic package 560.

The clock etalon 524 functions as a spectral filter. Its spectral features are periodic in frequency and spaced spectrally by a frequency increment, termed free spectral range (FSR), that is related to the refractive index of the constituent material of the clock etalon 524, which is fused silica in one example, and the physical length of the clock etalon 524. The etalon can alternatively be made of other high-index and transmissive materials such as silicon for compactness, but the optical dispersion of the material may need to be compensated for with additional processing inside the controller/DSP 505. Also, air-gap etalons, which are nearly dispersionless, are another alternative.

The contrast of the spectral features of the etalon is determined by the reflectivity of its opposed endfaces. In one example, reflectivity at the etalon endfaces is provided by the index of refraction discontinuity between the constituent material of the etalon and the surrounding gas or vacuum. In other examples, the opposed endfaces are coated with metal or preferably dielectric stack mirrors to provide higher reflectivity and thus contrast to the periodic spectral features.

In the illustrated example, the clock etalon 524 is operated in reflection. The FSR of the clock etalon is chosen based on the required scanning depth in an OCT system. The Nyquist criterion dictates that the periodic frequency spacing of the clock etalon that defines the sample rate be twice the largest frequency period component of the sample, thus setting the optical thickness of the clock etalon to twice the required imaging depth. However, as is typically done with clock oscillators, the periodic waveform can be electrically frequency doubled, tripled, etc, see doubler 528, or can be halved to obtain the desired sample rate while choosing an etalon of a length that is convenient for handling and that easily fits within the package 560 and on the bench 550. A thicker etalon compensates better for nonlinear frequency scanning than a thinner one due to its finer sample rate, but it is larger and more difficult to fabricate, so a tradeoff is made depending upon the laser tuning linearity, system depth requirements, and manufacturing tolerances. Moreover, a thicker etalon requires a laser of comparable coherence length to generate stable clock pulses, so the laser coherence length can also help dictate the design of the etalon thickness.

The light returning from the clock etalon 524 and not reflected by beamsplitter 522 is detected by detector 526. The light detected by detector 526 is characterized by drops and rises in power as the frequency of the tunable signal scans through the reflective troughs/reflective peaks provided by the clock etalon 524.

The detector photocurrent is amplified and conditioned. The clock signal is multiplied or divided in frequency by multiplier/divider 528, depending on the needs of the OCT system's application and the requirement for a convenient etalon (or other clock interferometer) size within the butterfly package 560. A digital delay line is also added to the doubler circuitry 528 is some embodiments to compensate for any round-trip optical delay to the probe 400.

The OCT signal that is transmitted through the input beam splitter 516 enters the detector subsystem 530. The detector subsystem 530 comprises an amplitude reference splitter 562 that directs a portion of the OCT signal, typically less than 10%, to an amplitude reference detector 564. This detector 564 is used to detect amplitude noise in the OCT signal.

Light transmitted through the amplitude reference splitter 562 passes through a parallel detector splitter 566, a polarization beam splitter 568 and is coupled onto OCT/Interference signal optical fiber 410 to the polarization dependent OCT probe 400 by output lens structure 518.

The returning interference signal from the OCT probe 400 is separated into its two polarizations by the polarization beam splitter 568. The portion of the interference signal that is perpendicular to the polarization of the OCT signal from the laser 510 is directed to and detected by a perpendicular interference signal detector 570. The portion of the interference signal that has a polarization that is parallel to the polarization of the polarization of the OCT signal from the laser 510 and that passed through the polarization beam splitter 568 is directed by the parallel detector splitter 566 and detected by the parallel interference signal detector 572.

The k-clock signal is used by the digital signal processing and analog-detector sampling system 505 as a sampling clock to trigger the sampling of the amplitude reference signal, the parallel detector signal, and the perpendicular detector signal. This information is used to perform the Fourier transform to reconstruct the image of the object including a polarization dependent OCT image at the two polarizations.

Figure 11B:
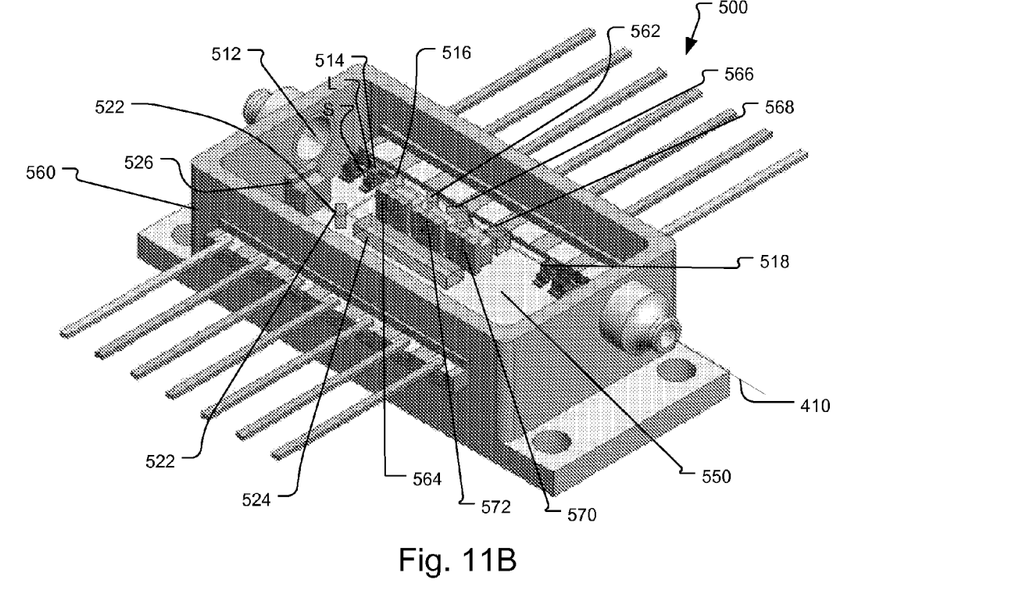
FIG. 11B is a perspective view of the integrated OCT engine according to the present invention.

FIG. 11B shows one physical implementation of the integrated polarization dependent OCT system 500 in a butterfly package 560. In this example, the lid of the package 560 is removed to expose the components of the bench 560. This view also shows the LIGA structures S that attach the lens substrates L to the bench 560.

Figure 12:
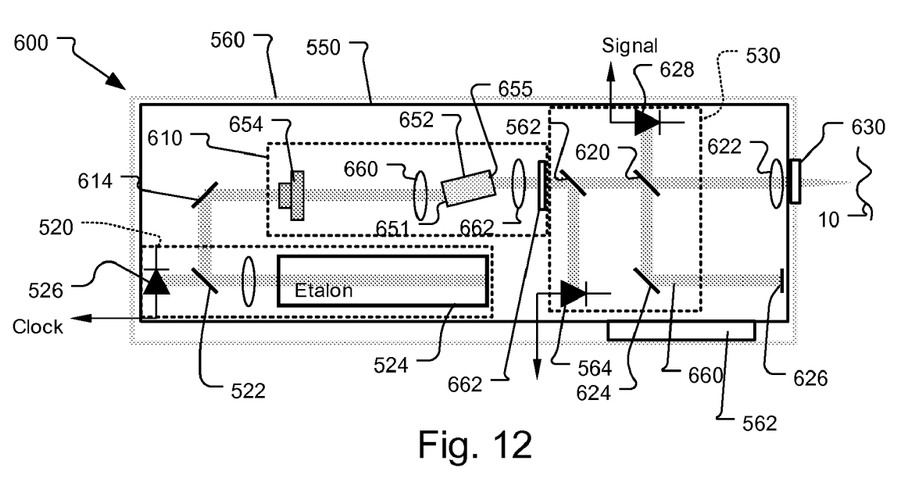
FIG. 12 is a schematic plan view of an integrated OCT engine/probe according to the present invention.

FIG. 12 shows another integrated OCT system 600 that has been constructed according to the principals of the present invention. This system integrates the swept source 610, k-clock system 520, detector system 530, and reference arm 660 on a bench 550, and within a hermetic package 560.

Generally the integrated laser clock system 600 comprises a tunable laser swept source subsystem 610, which generates a wavelength or frequency tunable OCT signal, a clock subsystem 520, which generates k-clock signals at spaced frequency increments as the tunable signals or emissions of the laser 610 are spectrally tuned over a spectral scan band, and a detector subsystem 530. The clock signals are generally used to trigger sampling of detector system.

The tunable laser subsystem 610, clock subsystem 520, and the detector subsystem 530 are integrated together on a common optical bench 550. This bench is termed a microoptical bench and is usually less than 20 mm by 30 mm and preferably less than 10 mm by 20 mm in size so that it fits within a standard butterfly or DIP (dual inline pin) hermetic package 560. In one implementation, the bench is fabricated from aluminum nitride. A thermoelectric cooler 562 is disposed between the bench 550 and the package 560 (attached/solder bonded both to the backside of the bench and inner bottom panel of the package 560) to control the temperature of the bench 550.

In more detail, the tunable laser 610 in the preferred embodiment in based on the tunable laser designs disclosed in U.S. Pat. No. 7,415,049 B2, which is incorporated herein in its entirety by this reference.

In the current implementation, the tunable laser 610 comprises a semiconductor gain chip 652 that is paired with a micro-electro-mechanical (MEMS) angled reflective Fabry-Perot tunable filter 654 to create external cavity laser (ECL) with the tunable filter 654 being an intracavity tuning element and forming one end, or back reflector, of a laser cavity of the tunable ECL.

The semiconductor optical amplifier (SOA) chip 652 is located within the laser cavity. In the current embodiment, both facets of the SOA chip 652 are angled relative to a ridge waveguide 58 running longitudinally along the chip 652 with the back facet 651 and the front facet 655 being anti-reflection (AR) coated. A partially reflecting substrate 662 provides reflectivity to define the front reflector of the laser cavity.

To collect and collimate the light exiting from each end facet of the SOA 652, two lens structures 660, 662 are used. Each lens structure 660, 662 comprises a LIGA mounting structure, which is deformable to enable post installation alignment, and a transmissive substrate in which the lens is formed. The transmissive substrate is typically solder or thermocompression bonded to the mounting structure, which in turn is solder bonded to the optical bench 550.

The first lens component 660 couples the light between the back facet of the SOA 652 and the tunable filter 654. Light exiting out the front facet of the SOA 652 is coupled by a second lens component 662 to the detector subsystem 530.

The angled reflective Fabry-Perot filter 654 is a multi-spatial-mode tunable filter having a curved-flat optical resonant cavity that provides angular-dependent, reflective spectral response back into the laser cavity. This effect is discussed in more detail in incorporated U.S. Pat. No. 7,415,049 B2. In the referred embodiment, the curved mirror is on the MEMS membrane and is on the side of the filter 654 that adjoins the laser cavity. The flat mirror is on the opposite side and faces the laser cavity. The flat mirror preferably has a higher reflectivity than the curved mirror. Currently the reflectivities for the flat and curved mirrors are typically 99.98% and 99.91%, respectively, in order to achieve the desired reflectivity and requisite linewidth of the filter 654 in reflection.

The light transmitted by the tunable filter 654 is coupled out of the laser cavity and into the clock subsystem 520 by fold mirror 614, which are reflective coated substrates that are solder bonded to the bench 550, fold the beam of the light from the tunable laser subsystem 610, allowing for a dimensionally compact system.

The light then passes to a beam splitter 522, which is preferably a 50/50 splitter to a clock etalon 524. Any light transmitted by the splitter 522 is preferably directed to a beam dump component that absorbs the light and prevents parasitic reflections in the hermetic package 560 and into the laser cavity and detectors.

The light returning from the clock etalon 524 is detected by detector 526 to form the k-clock signal.

The detector subsystem 530 receives the OCT signal from the tunable laser subsystem 610. The OCT signal passes through an amplitude reference splitter 562, and interference/reference splitter 620. The OCT signal is focused by an output lens 622 on the object of interest 10. The OCT signal exits the hermetic package 560 via a transmissive window 630 that is provided in the side of the package 560.

The OCT signal that is reflected by the interference/reference splitter 620 is directed to a reference arm 660 including reference arm fold mirror 624 to a reference arm mirror 626.

Light returning from the reference arm mirror 624 is mixed or combined with light from the sample 10, which is received by received by window 630 and focused by lens 622, at interference/reference splitter 620 to form the interference signal that is detected by interference signal detector 628.

Signal to noise ratio (SNR) improvement by reducing the effects of RIN is performed by digitally dividing the interference signal from detector 628 by the amplitude reference signal from detector 564 before FFT processing. This is a compact system for performing A-scans, but movement of the package 560 or the sample 10 would allow B-scans to be made. Additionally, a MEMS mirror scanner could be incorporated before the package's output lens to perform this function without movement of the sample or the package in some implementation.

While this invention has been particularly shown and described with references to preferred embodiments thereof, it will be understood by those skilled in the art that various changes in form and details may be made therein without departing from the scope of the invention encompassed by the appended claims.

What is claimed is:

1. A polarization sensitive optical coherence tomography probe, comprising:
    a probe body;
    an interference signal fiber coupler in the probe body that receives an optical coherence tomography (OCT) signal from a swept source laser of an OCT analysis system and divides the OCT signal between a reference optical fiber arm and a signal optical fiber arm;
    an optical window in the probe body through which the OCT signal from the signal optical fiber arm is transmitted to an object of interest and through which an object OCT signal is received from the object of interest and coupled into the signal optical fiber arm; and
    a polarization rotation element that rotates the polarization of the OCT signal from the reference optical fiber arm;
    wherein the object OCT signal is mixed with the OCT signal from the reference optical fiber arm to generate an interference signal that is transmitted from the probe body to the OCT analysis system, which comprises a polarization beam splitter for separating the interference signal into two polarizations, a parallel detector for detecting the interference signal that is polarized parallel to the OCT signal, and a perpendicular detector for detecting the interference signal that is polarized perpendicular to the OCT signal from the swept source laser.

2. A probe as claimed in claim 1, wherein the reference optical fiber arm comprises polarization maintaining optical fiber.

3. A probe as claimed in claim 2, wherein the signal optical fiber arm comprises polarization maintaining optical fiber.

4. A probe as claimed in claim 2, wherein the interference signal fiber coupler is a polarization maintaining coupler.

5. A probe as claimed in claim 1, wherein the polarization rotation element is a quarterwave plate.

* * * * *